United States Patent
Cottrell et al.

(10) Patent No.: US 8,921,621 B2
(45) Date of Patent: *Dec. 30, 2014

(54) PROCESS FOR THE PRODUCTION OF HCFC-1233ZD

(71) Applicant: Honeywell International Inc., Morristown, NJ (US)

(72) Inventors: Stephen A. Cottrell, Williamsville, NY (US); Hsueh Sung Tung, Getzville, NY (US); Konstantin A. Pokrovski, Orchard Park, NY (US); Haiyou Wang, Amherst, NY (US); Daniel C. Merkel, West Seneca, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/757,963

(22) Filed: Feb. 4, 2013

(65) Prior Publication Data
US 2013/0211154 A1 Aug. 15, 2013

Related U.S. Application Data

(60) Provisional application No. 61/598,938, filed on Feb. 15, 2012.

(51) Int. Cl.
| | |
|---|---|
| *C07C 17/25* | (2006.01) |
| *C07C 17/20* | (2006.01) |
| *C07C 21/18* | (2006.01) |
| *C07C 17/38* | (2006.01) |
| *C07C 17/383* | (2006.01) |
| *C07C 17/23* | (2006.01) |

(52) U.S. Cl.
CPC ............... *C07C 17/23* (2013.01); *C07C 17/20* (2013.01); *C07C 17/206* (2013.01); *C07C 17/38* (2013.01); *C07C 17/383* (2013.01); *C07C 17/25* (2013.01)
USPC ........... 570/155; 570/164; 570/177; 570/178; 570/216; 570/238; 570/263

(58) Field of Classification Search
None
See application file for complete search history.

(56) References Cited

U.S. PATENT DOCUMENTS

| | | |
|---|---|---|
| 6,018,084 A | 1/2000 | Nakada et al. |
| 6,023,004 A | 2/2000 | Thenappan et al. |

(Continued)

FOREIGN PATENT DOCUMENTS

| | | |
|---|---|---|
| EP | 0877009 A1 | 11/1998 |
| WO | WO 2010111067 A1 * | 9/2010 |

OTHER PUBLICATIONS

PCT ISR & Written Opinion issued in PCT/US2013/025523 dated May 10, 2013.

*Primary Examiner* — Jafar Parsa
*Assistant Examiner* — Medhanit Bahta
(74) *Attorney, Agent, or Firm* — Bruce O. Bradford

(57) ABSTRACT

A process for the manufacture of 1-chloro-3,3,3-trifluoropropene (HCFC-1233zd) at commercial scale from the reaction of HCC-240 and HF is disclosed. In one embodiment, HCC-240fa and HF are fed to a reactor operating at high pressure. Several different reactor designs useful in this process include; a stirred-tank reactor (batch and/or continuous flow); a plug flow reactor; a static mixer used as a reactor; at least one of the above reactors operating at high pressure; optionally combined with a distillation column running at a lower pressure; and combinations of the above; and/or with a distillation column. The resulting product stream consisting of 1233zd, HCl, HF, and other byproducts is partially condensed to recover HF by phase separation. The recovered HF phase is recycled to the reactor. The HCl is scrubbed from the vapor stream and recovered as an aqueous solution. The remaining organic components including the desired HCFC-1233zd are scrubbed, dried and distilled to meet commercial product specifications.

10 Claims, 1 Drawing Sheet

(56) References Cited

U.S. PATENT DOCUMENTS

| | | |
|---|---|---|
| 6,111,150 A | 8/2000 | Sakyu et al. |
| 6,362,383 B1 | 3/2002 | Wilmet et al. |
| 6,844,475 B1 * | 1/2005 | Tung et al. .................... 570/168 |
| 8,076,521 B2 | 12/2011 | Elsheikh et al. |
| 2005/0033097 A1 | 2/2005 | Tung et al. |
| 2005/0085674 A1 | 4/2005 | Nakada et al. |
| 2009/0018377 A1 * | 1/2009 | Boyce ........................... 570/165 |
| 2010/0056657 A1 | 3/2010 | Chen et al. |
| 2010/0181524 A1 | 7/2010 | Elsheikh et al. |
| 2010/0210882 A1 * | 8/2010 | Sharratt et al. ................. 570/142 |
| 2010/0256426 A1 | 10/2010 | Sakyu et al. |
| 2011/0218369 A1 | 9/2011 | Elsheikh et al. |
| 2011/0218370 A1 | 9/2011 | Elsheikh et al. |
| 2011/0232306 A1 | 9/2011 | Hulse et al. |
| 2011/0269999 A1 | 11/2011 | Cook et al. |
| 2012/0172636 A1 * | 7/2012 | Pokrovski et al. ............ 570/135 |

* cited by examiner

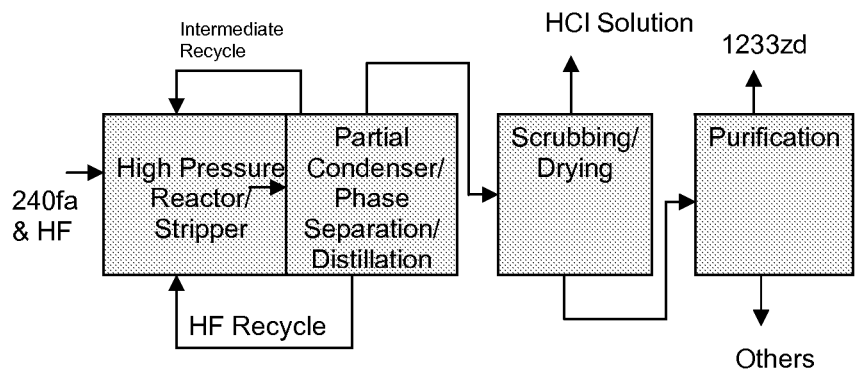

PROCESS FOR THE PRODUCTION OF HCFC-1233ZD

CROSS-REFERENCE TO RELATED APPLICATION

This application claims domestic priority under 35 U.S.C. 119(e) to commonly owned U.S. Provisional Application Ser. No. 61/598,938, filed 15 Feb. 2012, the disclosure of which is hereby incorporated herein by reference.

BACKGROUND OF THE INVENTION

This invention related to the production of 1-chloro-3,3,3-trifluoropropene (HCFC-1233zd) at commercial scale from the reaction of 1,1,1,3,3-pentachloropropane (HCC-240fa) and HF. HCFC-1233zd is a low global warming compound that has applications as a replacement for high global warming materials, for example in foam blowing and aerosol propellant applications.

The term HCFC-1233 is used herein to refer to all trifluoro, monochloro propenes, namely olefin compounds having the general formula $C_3H_2ClF_3$. The term HCFC-1233zd is used herein generically to refer to 1,1,1-trifluo-3, chloro-propene, independent of whether it is the cis form or the trans form. The terms "cis HCFC-1233zd" and "trans HCFC-1233zd" are used herein to describe the cis- and trans-forms of 1,1,1-trifluo-3-chlororopropene, respectively. The term "HCFC-1233zd" therefore includes within its scope cis HCFC-1233zd, trans HCFC-1233zd, and all combinations and mixtures of these. The designation "1233zd" is also used herein for these compounds.

U.S. Pat. No. 6,844,475 teaches a process for producing 1233zd from 240fa at low pressure and at temperatures lower than 150° C. The disclosure of this patent is hereby incorporated herein by reference.

U.S. Pat. No. 6,362,383 teaches a process for preparing 1,1,1,3,3-pentafluoro-propane (HFC-245fa) by (1) a first reaction step in which 1,1,1,3,3-pentachloropropane (HCC-240fa) is reacted with hydrogen fluoride in the liquid phase in the presence of a first hydrofluorination catalyst under conditions that are suitable for obtaining a mixture of reaction products comprising 1-chloro-3,3,3-trifluoropropene (HCFC-1233zd) in substantial amount, and (2) a second reaction step in which the 1-chloro-3,3,3-trifluoropropene (HCFC-1233zd) obtained from the first step is reacted with hydrogen fluoride in the liquid phase in the presence of a second hydrofluorination catalyst, and preferably while hydrogen chloride is continuously fed in, in order to obtain 1,1,1,3,3-pentafluoro-propane (HFC-245fa). The disclosure of this patent is hereby incorporated herein by reference.

SUMMARY OF THE INVENTION

The present invention provides a process for the manufacture of 1-chloro-3,3,3-trifluoropropene (HCFC-1233zd) at commercial scale, from the reaction of 1,1,1,3,3-pentachloropropane (HCC-240) and hydrogen fluoride (HF) in a liquid phase reactor. In certain embodiments the pressure range of the reaction is from 150 psig to 600 psig. In certain embodiments, a more preferred pressure range is from 230 psig to 500 psig and a most preferred pressure range is from 350 psig to 450 psig.

As used herein the term "liquid phase reactor" is used to designate one of the several different reactor designs that may be employed in this process, including:

1. stirred-tank reactor (batch and/or continuous flow);
2. plug flow reactor;
3. static mixer used as a reactor;
4. one of the above reactors operating at high pressure; optionally combined with a distillation column running at a lower pressure; and
5. combinations of the above; and/or with a distillation column.

In one embodiment of the process, HCC-240fa and HF are fed to a liquid phase reactor operating at high pressure. The resulting product stream consisting of 1233zd, HCl, HF, and other byproducts is partially condensed to recover HF by phase separation. The recovered HF phase is recycled to the reactor. The HCl is scrubbed from the vapor stream and recovered as an aqueous solution. The remaining organic components including the desired HCFC-1233zd are scrubbed, dried and distilled to meet commercial product specifications.

BRIEF DESCRIPTION OF THE DRAWING

FIG. 1 illustrates one embodiment of the process steps of the present invention.

DETAILED DESCRIPTION OF THE INVENTION

Referring to FIG. 1, a preferred embodiment of the present invention can be generally described as a process for the production of HCFC-1233zd from HCC-240fa and HF, with or without a catalyst at commercial scale. The detailed steps of this process are as follows:

(1) High pressure liquid phase reaction of HCC-240 and HF, with or without a catalyst, forming HCFC-1233zd, its byproducts, HCl and unreacted HF.
(2) Partial condensation of the effluent stream from the reaction step.
(3) Phase separation of the condensate from Step (2) to form an HF-rich layer and an organic rich layer.
(4) Recycle of the HF-rich layer from Step (3) to the reactor.
(5) The organic layer from Step (3) is fed to an HCl recovery system to remove and recover HCl as a solution in water. A distillation step may be included to purify the HCl.
(6) The HCl-free organic components from Step (5) are distilled to remove recyclable intermediates to HCFC-1233zd.
(7) The recyclable intermediates from Step (6) are fed back to the reactor of Step (1).
(8) The overhead stream from Step (6) is fed to a caustic scrubber to remove any remaining acidity and dried with an appropriate drying agent such as sulfuric acid or molecular sieves.
(9) The acid-free, dry stream from Step (8) is distilled to produce HCFC-1233zd meeting all product specifications.

If desired, the process steps may be modified such that HF is removed in Steps (2) and (3), for example, by using absorption in sulfuric acid.

As described above, in one embodiment of the process, HCC-240fa and HF are fed to a reactor operating at high pressure. The resulting product stream consisting of 1233zd, HCl, HF, and other byproducts is partially condensed to recover HF by phase separation. The recovered HF phase is recycled to the reactor. The HCl is scrubbed from the vapor stream and recovered as an aqueous solution. The remaining organic components including the desired HCFC-1233zd are scrubbed, dried and distilled to meet commercial product specifications.

Step (1):

As described above, the high pressure liquid phase reaction of HCC-240 and HF, with or without a catalyst, yields a product stream comprising HCFC-1233zd, byproducts, HCl and unreacted HF. As described above, in certain embodiments the pressure range is from 150 psig to 600 psig. In certain embodiments, a more preferred pressure range is from 230 psig to 500 psig and a most preferred pressure range is from 350 psig to 450 psig.

In certain embodiments, the catalyst choices are selected from known Lewis acid catalysts. The preferred catalysts are $TiCl_4$ or $SbCl_5$, with $TiCl_4$ being more preferred. In certain embodiments, the most preferred choice is operation of the reactor without employing any catalyst.

The typical byproducts observed in the reaction stream are precursors to 1233zd such as 241fa, 242fa, and 243fa. These can easily be separated from the reaction stream using known techniques and recycled.

Step (2):

As described above, this step entails the partial condensation of the effluent stream from the reaction in Step (1). In certain embodiments, the condensation takes place using a low-temperature refrigerant brine at temperatures ranging from −80° C. to ambient. The pressure is appropriate to allow for condensation at the chosen temperature while allowing the HCl to remain as a vapor.

Step (3):

As described above, this step entails the phase separation of the condensate from Step (2) to form an HF-rich layer and an organic rich layer. In certain embodiments, the phase separation takes place in a vessel appropriate to allow for separation of the organic and HF phases such as a simple horizontal tank. The phase separation takes place at a similar temperature and pressure as the condensation of the previous step.

Step (4):

As described above, this step entails the recycle of the HF-rich layer from Step (3), back to the reactor in Step (1). In certain embodiments, the HF-layer is collected in a vessel and fed continuously back to the reactor of Step (1).

Step (5):

As described above, this step entails the feeding of the organic layer from Step (3) to an HCl recovery system to remove and recover HCl as a solution in water. A distillation step may be included to purify the HCl. In certain embodiments, the HCl is recovered using a packed-bed scrubber and falling-film absorber to form a high-strength solution that may be sold or used as a raw material for other processes, such as the production of calcium chloride. Optionally, the HCl may be distilled in a simple distillation column using a low-temperature cooling medium (−40° C. to −100° C.) to obtain a stream that is essentially-free of HF, which may be more desirable as a saleable product.

Step (6):

As described above, in this step the HCl-free organic components from Step (5) are distilled to remove recyclable intermediates to HCFC-1233zd. In certain embodiments the materials distilled are higher-boiling precursors to 1233zd such as 241fa and 242fa. These materials may be present in ranges of 1-20% of the crude 1233zd stream.

Step (7):

As described above, in this step the recyclable intermediates from Step (6) are fed back to the reactor in Step (1). In certain embodiments, one or more of the materials described above are subjected to the recycling to the reactor of Step (1). In certain embodiments, all of the recovered materials are recycled to the reactor of Step (1).

Step (8):

As described above, in this step the overhead stream from Step (6) is fed to a caustic scrubber to remove any remaining acidity and dried with an appropriate drying agent such as sulfuric acid or molecular sieves. In certain embodiments, the drying agents that are appropriate may be selected from known materials such as: 3 A to 5 A molecular sieves, high strength sulfuric acid, calcium sulfate and silica gels. In certain embodiments, the caustic scrubber consists of a packed-tower with a circulating solution of NaOH or KOH.

Step (9):

As described above, in this step the acid-free, dry stream from Step (8) is distilled to produce HCFC-1233zd, meeting all commercial product specifications. In certain embodiments, commercial product specifications include a GC purity of 99.5% or greater, with low levels, e.g., less than 100 ppm, of unsaturated compounds.

Optionally, the stream leaving the reactor can first have the HCl removed, prior to the phase separation and recycle of HF. Also, phase separation is not necessarily the only removal technique for HF. Other known techniques can be used, for example, sulfuric acid absorption, and the like.

Example 1

10 lb/hr of HF and 10 lb/hr of HCC-240 are fed to a stirred 50 gallon reactor operating at a pressure of 230 psig and a temperature of 117° C. Product vapor consisting mainly of 1233zd, HF, HCl, 241fa, 242fa, 234fa, 244fa, and 245fa, exit the system from the top of a distillation column on top of the reactor vessel. The vapor stream enters a partial condenser operating at −30° C. where the organic components and HF are condensed and the HCl continues as a vapor. The liquid stream from the partial condensation enters a phase separation vessel operating at −10° C.

In the phase separation vessel, a top phase consisting of mainly HF and a bottom phase consisting of mainly organic are seen. The HF phase is recycled back to the reaction vessel. The bottom organic phase is vaporized and joins the vapor HCl stream from the partial condensation. The pressure of the stream is in the range of 2 psig to 15 psig. The vapor stream enters a water absorption system where the HCl is separated from the other components in a high strength solution (32% to 28%). The components that are not absorbed in the HCl solution are fed to a circulating caustic scrubber to remove trace acidic component and are subsequently fed to a column containing 3 A molecular sieves to remove moisture. The dried crude organic stream is condensed and fed to a series of two distillation columns. The first column removes components that boil higher than 1233zd such as 241fa, and 242fa. These materials are recycled back to the reactor. The second column removes light boiling components. These materials are disposed of appropriately. The product stream consisting of 1233zd at a purity of 99.5%, or higher is collected and stored.

Example 2

HCC-240 and HF are fed to a stirred-tank reactor operating at 400 psig. HFCO-1233zd and HCl are produced at high conversion.

Example 3

HCC-240 and HF are fed to a plug flow reactor operating at 400 psig. HFCO-1233zd and HCl are produced at high conversion.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the production of 1-chloro-3,3,3-trifluoropropene (HCFC-1233zd) comprising the steps of:
   (a) reacting HCC-240 and HF in a high pressure liquid phase reactor wherein the reactor pressure range is from 400 psig to 600 psig to generate an effluent reaction stream comprising HCFC-1233zd, intermediates and byproducts of HCFC-1233zd, HCl and unreacted HCC-240 and HF; and
   (b) at least partially condensing the effluent stream from reaction step (a) to form a condensate comprising HCFC-1233zd;
   (c) separating the condensate from step (b) using phase separation, to form an HF-rich layer and an organic rich layer;
   (d) recycling the HF-rich layer from step (c) to the reactor in step (a);
   (e) feeding the organic rich layer from step (c) to an aqueous HCl recovery system to remove and recover the HCl as a solution in water;
   (f) distilling the HCl-free organic components from step (e) to form an overhead stream and to remove any recyclable intermediates to HCFC-1233zd;
   (g) recycle the intermediates to HCFC-1233zd from step (f) by feeding them back to the reactor of step (a);
   (h) feeding the overhead stream from step (f) to a caustic scrubber to remove any remaining acidity and drying the scrubbed stream with a drying agent; and
   (i) distilling the acid-free, dry stream from step (h) to produce high purity HCFC-1233zd having a GC purity of 99.5% or greater.

2. The process of claim 1, wherein the reactor pressure range is from 400 psig to 500 psig.

3. The process of claim 1, wherein the reactor pressure range is about 450 psig.

4. The process of claim 1, where step (a) is performed in a stirred-tank reactor operating in batch mode.

5. The process of claim 1, where step (a) is performed in a stirred-tank reactor operating in continuous flow mode.

6. The process of claim 1, where step (a) is performed in a plug flow reactor.

7. The process of claim 1, where step (a) is performed in a static mixer used as a reactor.

8. The process of claim 1, where step (a) is also performed with a distillation column running at a pressure less than the reactor pressure.

9. The process of claim 1, where step (a) is performed in a stirred-tank reactor operating at 400 psig.

10. The process of claim 1, where step (a) is performed in a plug flow reactor operating at 400 psig.

* * * * *